(12) United States Patent
Gotanda (10) Patent No.: US 11,344,275 B2
(45) Date of Patent: May 31, 2022

(54) MEDICAL DIAGNOSTIC-IMAGING APPARATUS

(71) Applicant: CANON MEDICAL SYSTEMS CORPORATION, Otawara (JP)

(72) Inventor: Katsumi Gotanda, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 60 days.

(21) Appl. No.: 16/865,538

(22) Filed: May 4, 2020

(65) Prior Publication Data

US 2020/0367851 A1     Nov. 26, 2020

(30) Foreign Application Priority Data

May 22, 2019  (JP) .............................. JP2019-095653
Apr. 9, 2020  (JP) .............................. JP2020-070168

(51) Int. Cl.
*A61B 6/00*  (2006.01)
*A61B 6/04*  (2006.01)
*A61B 6/03*  (2006.01)

(52) U.S. Cl.
CPC .............. *A61B 6/548* (2013.01); *A61B 6/032* (2013.01); *A61B 6/0407* (2013.01);
(Continued)

(58) Field of Classification Search
CPC ... A61B 2560/04; A61B 6/032; A61B 6/0407; A61B 6/102; A61B 6/4447; A61B 6/5205; A61B 6/542; A61B 6/548; A61B 6/0487; A61B 6/4085; A61B 6/547; A61B 6/583; A61B 5/055; A61B 6/027; A61B 6/0414; A61B 6/0442; A61B 6/502; A61B 6/5276; A61B 10/0233; A61B 2090/376; A61B 34/30; A61B 6/02; A61B 6/035; A61B 6/0421; A61B 6/0435; A61B 6/0478;
(Continued)

(56) References Cited

U.S. PATENT DOCUMENTS 5,402,462 A * 3/1995 Nobuta ................ A61B 6/0487
                                                   378/20
9,326,907 B2 * 5/2016 Marie .................. A61B 6/4494
(Continued)

FOREIGN PATENT DOCUMENTS

JP     2004-208954 A     7/2004
JP     2005-296469 A    10/2005
(Continued)

*Primary Examiner* — Irakli Kiknadze
(74) *Attorney, Agent, or Firm* — Oblon, McClelland, Maier & Neustadt, L.L.P.

(57) ABSTRACT

A medical diagnostic-imaging apparatus according to an embodiment includes a gantry device and a processing circuitry. The gantry device includes an opening in which a subject is inserted. The processing circuitry is configured to set an inserting range indicating a range in which the subject is inserted into the opening by move of the subject or by move of the gantry device based on a scan plan. The processing circuitry is configured to acquire a position of the subject in the inserting range as first position information. The processing circuitry is configured to determine whether the subject interferes with the gantry device based on the first position information.

13 Claims, 9 Drawing Sheets

(52) U.S. Cl.
CPC .......... *A61B 6/4447* (2013.01); *A61B 6/5205* (2013.01); *A61B 2560/04* (2013.01)

(58) Field of Classification Search
CPC ..... A61B 6/04; A61B 2034/305; A61B 34/71; A61B 6/4007; A61B 6/4014; A61B 6/4441; A61B 6/4458; A61B 6/4464; A61B 6/5235; A61B 5/004; A61B 6/4488; A61B 6/461; A61B 6/488; A61B 6/4435; A61B 6/545; A61B 5/704; A61B 6/08; A61B 6/467; A61N 5/1049; A61N 5/107; A61N 2005/105; A61N 2005/1061; A61N 2005/1059; A61N 2005/1074; A61N 5/1067; A61N 5/1081; A61N 2005/1054; A61N 2005/1094; A61N 5/1042; A61N 5/1082; A61N 5/1037; A61N 5/1068; A61N 5/1048; A61N 5/1064; A61N 2005/1089; A61N 5/1065; A61N 5/01; A61N 5/1083; A61N 5/1016; A61N 7/02; G06T 2207/10081; G06T 11/005; G06T 11/006; G06T 15/503; G06T 2207/10088; G06T 2207/10132; G06T 2207/20221; G06T 2207/30004; G06T 7/0012; G06T 7/74; G06T 11/003; G06T 11/008; G06T 2207/10028; G06T 2207/10104; G06T 2207/10116; G06T 2207/10121; G06T 2207/20076
USPC ......................................... 378/4, 20, 68, 208
See application file for complete search history.

(56) References Cited

U.S. PATENT DOCUMENTS

| | | | |
|---|---|---|---|
| 10,265,042 B2 * | 4/2019 | Stoutenburgh | A61B 6/542 |
| 11,058,319 B2 * | 7/2021 | Boettger | A61B 5/055 |
| 2014/0098934 A1 * | 4/2014 | Kondo | A61B 6/032 378/20 |
| 2017/0105696 A1 | 4/2017 | Gotanda et al. | |
| 2018/0140270 A1 * | 5/2018 | Profio | A61B 6/4435 |
| 2018/0168528 A1 * | 6/2018 | Ozawa | A61B 6/12 |

FOREIGN PATENT DOCUMENTS

| | | |
|---|---|---|
| JP | 2006-187515 A | 7/2006 |
| JP | 2017-77457 A | 4/2017 |

* cited by examiner

MEDICAL DIAGNOSTIC-IMAGING APPARATUS

CROSS-REFERENCE TO RELATED APPLICATIONS

This application is based upon and claims the benefit of priority from Japanese Patent Application No. 2019-095653, filed on May 22, 2019; and Japanese Patent Application No. 2020-070168, filed on Apr. 9, 2020, the entire contents of all of which are incorporated herein by reference.

FIELD

Embodiments described herein relate generally to a medical diagnostic-imaging apparatus.

BACKGROUND

In medical diagnostic-imaging apparatuses, such as X-ray computed tomography (CT) apparatuses, a subject is laid on a couchtop of a couch device and brought into a gantry device by moving the couchtop, and imaging of the subject is thus performed. In imaging with the X-ray CT apparatuses, there is a case requiring suspension or retake when a subject and a gantry device interfere with each other. In this case, the subject is exposed to unnecessary radiation.

DETAILED DESCRIPTION

A medical diagnostic-imaging apparatus according to an embodiment includes a gantry device and a processing circuitry. An opening into which a subject is inserted is included. The processing circuitry is configured to set an inserting range indicating a range in which the subject is inserted into the opening by move of the subject or by move of the gantry device based on a scan plan. The processing circuitry is configured to acquire a position of the subject in the inserting range as first position information. The processing circuitry is configured to determine whether the subject interferes with the gantry device based on the first position information.

Hereinafter, embodiments of a medical diagnostic-imaging apparatus will be described in detail, referring to the accompanying drawings.

First Embodiment

A medical diagnostic-imaging apparatus is an apparatus that performs an examination by imaging a subject (for example, patient), and the like. The medical diagnostic-imaging apparatus includes an X-ray CT apparatus, a magnetic resonance imaging (MRI) apparatus, a nuclear-medicine diagnostic apparatus, and the like. The present embodiment will be described with an X-ray CT apparatus as an example.

Figure 1:
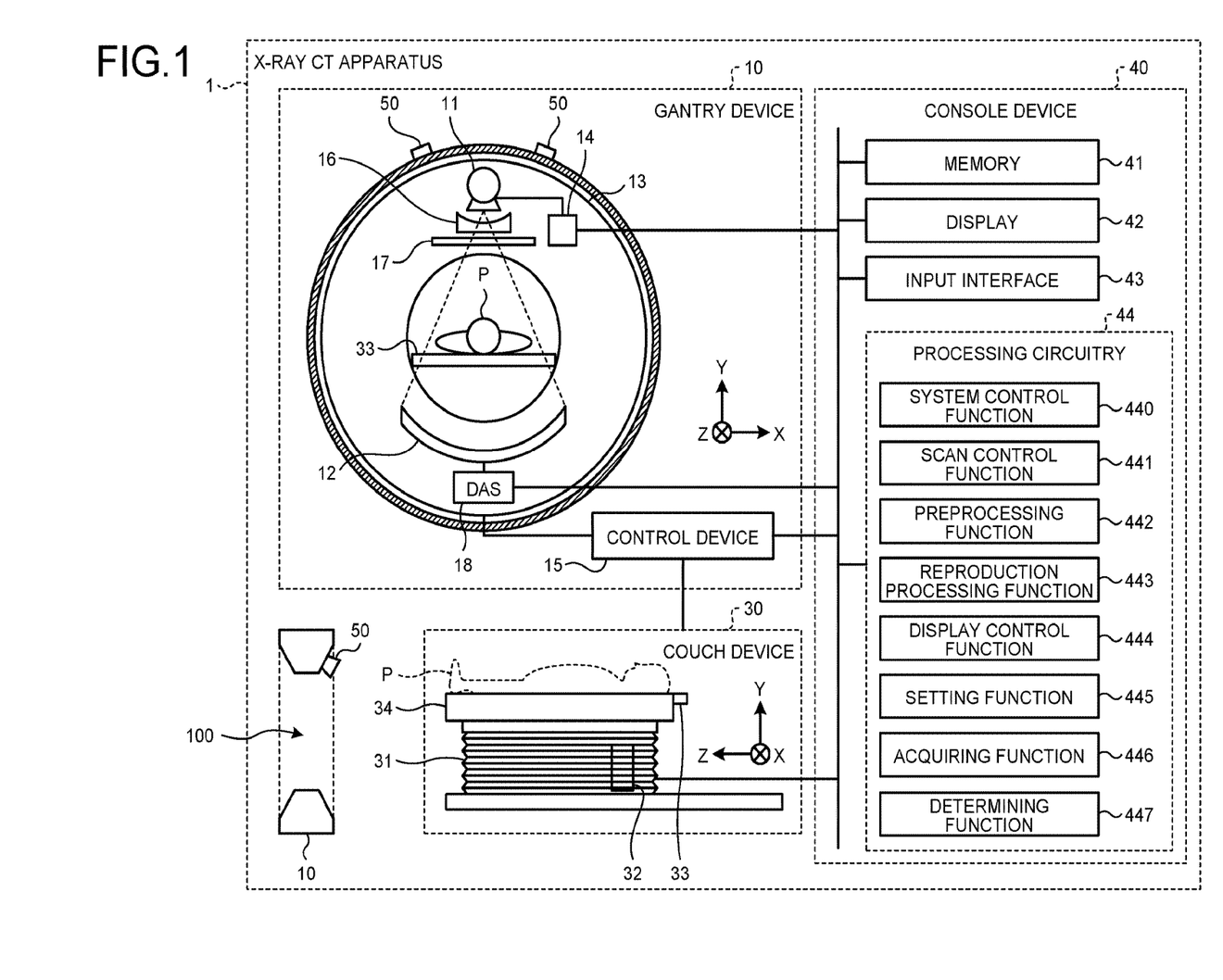
FIG. 1 illustrates an example of a configuration of an X-ray CT apparatus according to a first embodiment.

FIG. 1 illustrates an example of a configuration of an X-ray CT apparatus 1 according to a first embodiment. The X-ray CT apparatus 1 collects CT image data of a subject. Specifically, the X-ray CT apparatus 1 collects projection data by rotating an X-ray tube and an X-ray detector about the subject at substantially the center of rotation, to detect an X-ray that has passed through the subject. The X-ray CT apparatus 1 then generates CT image data based on the collected projection data. As illustrated in FIG. 1, the X-ray CT apparatus 1 according to the first embodiment includes a gantry device 10, a couch device 30, and a console device 40.

In the present embodiment, a rotation axis of a rotating frame in a non-tilted state, or a direction of length of a couchtop 33 of the couch device 30 is denoted as the Z-axis direction. Moreover, a direction of axis that is orthogonal to the Z-axis direction, and that is horizontal to a floor surface is denoted as the X-axis direction. Furthermore, a direction of axis that is orthogonal to the Z-axis direction, and that is perpendicular to the floor surface is denoted as the Y-axis direction. FIG. 1 illustrates the gantry device 10 from plural directions for explanation, and shows a case in which the X-ray CT apparatus 1 has a single unit of the gantry device 10.

The gantry device 10 includes an X-ray tube 11, an X-ray detector 12, a rotating frame 13, an X-ray high-voltage device 14, a control device 15, a wedge 16, a collimator 17, and a data acquisition system (DAS) 18.

The X-ray tube 11 is a vacuum tube including a cathode (filament) that generates a thermion, and an anode (target) that receives collision of thermions to generate an X-ray. The X-ray tube 11 generates an X-ray to be irradiated to a subject P by irradiating thermions from the cathode to the anode by application of a high voltage from the X-ray high-voltage device 14. For example, the X-ray tube 11 includes a rotating anode X-ray tube that is capable of generating X-rays by irradiating thermions to the rotating anode.

The wedge 16 is a filter to adjust an amount of X-ray emitted from the X-ray tube 11. Specifically, the wedge 16 is a filter that lets an X-ray emitted from the X-ray tube 11 to pass through to attenuate it such that the X-ray to be irradiated to the subject P from the X-ray tube 11 has a predetermined distribution. For example, the wedge 16 is a wedge filter or a bow-tie filter, and is a filter obtained by processing aluminum or the like to have a predetermined target angle and a predetermined thickness.

The collimator 17 is a lead plate or the like to narrow an irradiation range of X-rays that have passed through the wedge 16, and forms a slit by combination of plural lead plates, or the like. The collimator 17 is also called X-ray aperture. Moreover, FIG. 1 shows a case in which the wedge 16 is arranged between the X-ray tube 11 and the collimator 17, but the collimator 17 may be arranged between the X-ray tube 11 and the wedge 16. In this case, the wedge 16 lets X-rays, the irradiation range of which have been controlled by the collimator 17 pass through, to attenuate them.

The X-ray detector 12 has plural detecting devices that detect X-rays. The respective detecting devices in the X-ray detector 12 detect X-rays that have emitted from the X-ray tube 11 and have passed through the subject P, and the X-ray detector 12 outputs a signal corresponding to the amount of detected X-ray to the DAS 18. The X-ray detector 12 has plural rows of detecting devices in which plural detecting devices are arranged along an arc about a focal point of the X-ray tube 11 in a channel direction. The X-ray detector 12 has, for example, a structure in which plural detecting-device rows in which the detecting devices arranged in the channel direction are arranged in a slicing direction (direction of rows).

For example, the X-ray detector 12 is an indirection conversion detector that includes a grid, a scintillator array, and an optical sensor array. The scintillator array includes plural scintillators. The scintillator includes a scintillator crystal that outputs light having photons in an amount corresponding to an amount of incident X-ray. The grid is arranged on a surface on an X-ray incident side of the scintillator array, and includes an X-ray shielding plate that absorbs scattered X-rays. The grid is also called a collimator (one-dimensional collimator or two-dimensional collimator). The optical sensor array has a function of converting into an electrical signal according to an amount of light from the scintillator, and includes, for example, an optical sensor, such as photodiode. The X-ray detector 12 may also be a direct conversion detector that includes a semiconductor device converting an incident X-ray into an electrical signal.

The X-ray high-voltage device 14 includes electrical circuits, such as transformer and rectifier, and includes a high-voltage generating device that generates a high voltage to be applied to the X-ray tube 11, and an X-ray control device that controls an output voltage according to an X-ray generated by the X-ray tube 11. The high-voltage generating device may be of a transformer type, or may be of an inverter type. The X-ray high-voltage device 14 may be arranged in the rotating frame 13, or may be arranged in a fixing frame not shown. The fixing frame is a frame that rotatably supports the rotating frame 13.

The DAS 18 collects a signal of an X-ray detected by the respective detecting devices in the X-ray detector 12. For example, the DAS 18 includes an amplifier that subjects an electrical signal output from each of the detecting devices to amplification processing, and an analog-to-digital (A/D) converter that converts the electrical signal into a digital signal, and generates detection data. The DAS 18 is implemented by, for example, a processor.

The rotating frame 13 supports the X-ray tube 11 and the X-ray detector 12 so as to oppose to each other, and is a ring-shaped frame that rotates the X-ray tube 11 and the X-ray detector 12 by the control device 15. For example, the rotating frame 13 is a casting made from aluminum. The rotating frame 13 can support the X-ray high-voltage device 14, the wedge 16, the collimator 17, the DAS 18, and the like also, in addition to the X-ray tube 11 and the X-ray detector 12. Furthermore, the rotating frame 13 can support various components not shown in FIG. 13 also.

The data generated by the DAS 18 is transmitted to a receiver that is arranged at a non-rotating portion (for example, the fixing frame, or the like, and illustration thereof is omitted in FIG. 1) of the gantry device 10 and that has a photodiode from a transmitter that is arranged in the rotating frame 13 and that has a light emitting diode (LED) by optical communication, to be transferred to the console device 40. The data transmission method from the rotating frame 13 to the non-rotating portion of the gantry device 10 is not limited to optical communication. Any of non-contact data transmission method may be applied, and a contact data transmission method may be applied.

The control device 15 includes a processing circuitry that has a central processing unit (CPU) or the like, and a driving mechanism, such as a motor and an actuator. The control device 15 performs motion control of the gantry device 10 and the couch device 30. For example, the control device 15 controls rotation of the rotating frame 13, tilt of the gantry device 10, movement of the couch device 30 and the couchtop 33, and the like. As an example, the control device 15 rotates the rotating frame 13 about an axis parallel to the X-axis direction based on input tilt angle information, as a control to tilt the gantry device 10. The control device 15 may be arranged in the gantry device 10, or may be arranged in the console device 40.

As illustrated in FIG. 1, a position sensor 50 is provided in the gantry device 10. Processing of the position sensor 50 will be described later.

The couch device 30 is equipment to put the subject to be imaged thereon, and to move the subject P, and includes a base 31, a couch driving device 32, the couchtop 33, and a supporting frame 34. The base 31 is a casing that supports the supporting frame 34 movably in a vertical direction. The couch driving device 32 is a driving mechanism that moves the couchtop 33 on which the subject P is laid in a direction of length of the couchtop 33, and includes a motor, an actuator, and the like. The couchtop 33 arranged on an upper surface of the supporting frame 34 is a plate on which the subject P is laid. The couch driving device 32 may move the supporting frame 34 in the direction of length of the couchtop 33 in addition to the couchtop 33.

The console device 40 includes a memory 41, a display 42, an input interface 43, and a processing circuitry 44. The console device 40 will be described as an independent unit separated from the gantry device 10, but the console device 40 or a part of the respective components of the console device 40 may be included in the gantry device 10.

The memory 41 is implemented by a semiconductor memory device, such as a random access memory (RAM) and a flash memory, a hard disc, an optical disc, and the like. The memory 41 stores, for example, projection data and CT image data. Moreover, for example, the memory 41 stores a program enabling a circuit included in the X-ray CT apparatus 1 to implement a function. The memory 41 may be implemented by a server group (cloud) connected with the X-ray CT apparatus 1 through a network.

The display 42 displays various kinds of information. For example, the display 42 displays various kinds of images generated by the processing circuitry 44, or a graphical user interface (GUI) to receive various kinds of operations from an operator. For example, the display 42 is a liquid crystal display or a cathode ray tube (CRT) display. The display 42 may be structured as a desktop unit, or may be structured as a tablet terminal or the like that can communicate wirelessly with a main unit of the console device 40.

The input interface 43 receives various kinds of input operations from the operator, and converts the received input operation into an electrical signal, to output to the processing circuitry 44. For example, the input interface 43 receives an input operation of reconstruction conditions at the time of reconstructing CT image data, image processing conditions at the time of generating post-processing image from the CT image data, and the like from the operator. For example, the input interface 43 is implemented by a mouse, a keyboard, a trackball, a switch, a button, an joystick, a touchpad to which an input operation is made by touching an operating surface, a touch screen in which a display screen and a touch pad are integrated, a non-contact input circuit using an optical sensor, a voice input circuit, and the like. The input interface 43 may be arranged in the gantry device 10. Furthermore, the input interface 43 may be composed of a tablet terminal that can communicate wirelessly with the main unit of the console device 40, or the like. Moreover, the input interface 43 is not limited to ones having a physical part, such as a mouse and a keyboard. For example, a processing circuitry that receives an electrical signal corresponding to an input operation from an external input device provided separately from the console device 40, and that outputs the electrical signal to the processing circuitry 44 is also included in examples of the input interface 43.

The processing circuitry 44 controls overall operation of the X-ray CT apparatus 1. For example, the processing circuitry 44 performs a system control function 440, a scan control function 441, a preprocessing function 442, a reconstruction processing function 443, and a display control function 444.

The system control function 440 controls various kinds of functions of the processing circuitry 44 based on an input operation received from the operator through the input interface 43.

The scan control function 441 performs scanning using X-rays with respect to the subject P. For example, the scan control function 441 controls scanning based on an input operation received from the operator through the input interface 43. Specifically, the scan control function 441 controls an output voltage from the high-voltage generating device by transmitting a control signal to the X-ray high-voltage device 14 based on the input operation. Moreover, the scan control function 441 controls data collection by the DAS 18 by transmitting a control signal to the DAS 18.

The preprocessing function 442 generates data subject to preprocessing by performing preprocessing with respect to X-ray detection data transmitted from the DAS 18. Specifically, the preprocessing function 442 generates data subjected to preprocessing, by performing correction processing, such as logarithmic conversion processing, offset correction, sensitivity correction, and beam hardening correction. Data before preprocessing (X-ray detection data) and data subjected to preprocessing may be collectively called projection data.

The reconstruction processing function 443 generates CT image data by reconstructing projection data generated by the preprocessing function 442, by applying various kinds of reconstruction methods (for example, back projection such as filtered back projection (FBP), interactive approximation, and the like). Furthermore, the reconstruction processing function 443 stores generated CT image data in the memory 41.

The display control function 444 displays various kinds of images generated by the processing circuitry 44 on the display 42. For example, the display control function 444 displays CT image data generated by the reconstruction processing function 443 on the display 42. The display control function 444 is an example of a notifying unit.

Furthermore, for example, the processing circuitry 44 performs a setting function 445, an acquiring function 446, and a determining function 447. Processing of the setting function 445, the acquiring function 446, and the determining function 447 will be described later. The setting function 445 is an example of a setting unit. The acquiring function 446 is an example of an acquiring unit. The determining function 447 is an example of a determining unit.

In the X-ray CT apparatus 1 illustrated in FIG. 1, the respective functions are stored in the memory 41 in a form of computer-executable programs. The processing circuitry 44 is a processor that implements a function corresponding to each program by reading and executing a program from the memory 41. In other words, the processing circuitry 44 that has read the respective programs is to have functions corresponding to the read programs.

The term "processor" used in the above description signifies, for example, a circuit such as a CPU, a graphics processing unit (GPU), an application specific integrated circuit (ASIC), a programmable logic device (for example, a simple programmable logic device (SPLD), and a complex programmable logic device (CPLD)), and a field programmable gate array (FPGA). The processor reads and executes a program stored in a storage circuit, and thereby implements a function. It may be configured to install the program directly in a circuit in the processor, instead of storing the program in the storage circuit. In this case, the processor implements a function by reading and executing the program installed in the circuit. The respective processors of the present embodiment are not limited to be configured as a single circuit per processor, but plural independent circuits may be combined to configure one processor to implement its function.

The overall configuration of the X-ray CT apparatus 1 according to the present embodiment has been described. In the X-ray CT apparatus 1, the subject P is laid on the couchtop 33 of the couch device 30, the couchtop 33 is moved to send the subject into the gantry device 10, and imaging of the subject P is performed. When the subject P interferes with the gantry device 10, there is a case requiring suspension of imaging or retake. For example, when the subject P moves before the subject P is sent into the inside of the gantry device 10 to change the position of the subject P, suspension of imaging or retake becomes necessary. In this case, unnecessary exposure occurs.

Accordingly, the X-ray CT apparatus 1 according to the present embodiment performs following processing to prevent interference between the subject P and the gantry device 10. The X-ray CT apparatus 1 according to the present embodiment includes the gantry device 10, the setting function 445, the acquiring function 446, and the determining function 447. The gantry device 10 has an opening 100 (refer to FIG. 1) into which the subject P is inserted. The setting function 445 sets an inserting range that indicates a range into which the subject P is inserted into the opening 100 of the gantry device 10 by move of the subject P based on a scan plan. The acquiring function 446 acquires a position of the subject P in the inserting range as first position information. The determining function 447 determines whether the subject P interferes with the gantry device 10 based on the first position information. Specifically, the inserting range indicates a range into which the subject P is inserted into the opening 100 by move of the couchtop 33 of the couch device 30 on which the subject P is laid. Moreover, the determining function 447 further performs adjustment of the position of the couchtop 33 based on a result of determination.

Next, the respective functions of the setting function 445, the acquiring function 446, and the determining function 447 performed by the processing circuitry 44 in the first embodiment will be described.

Figure 2:
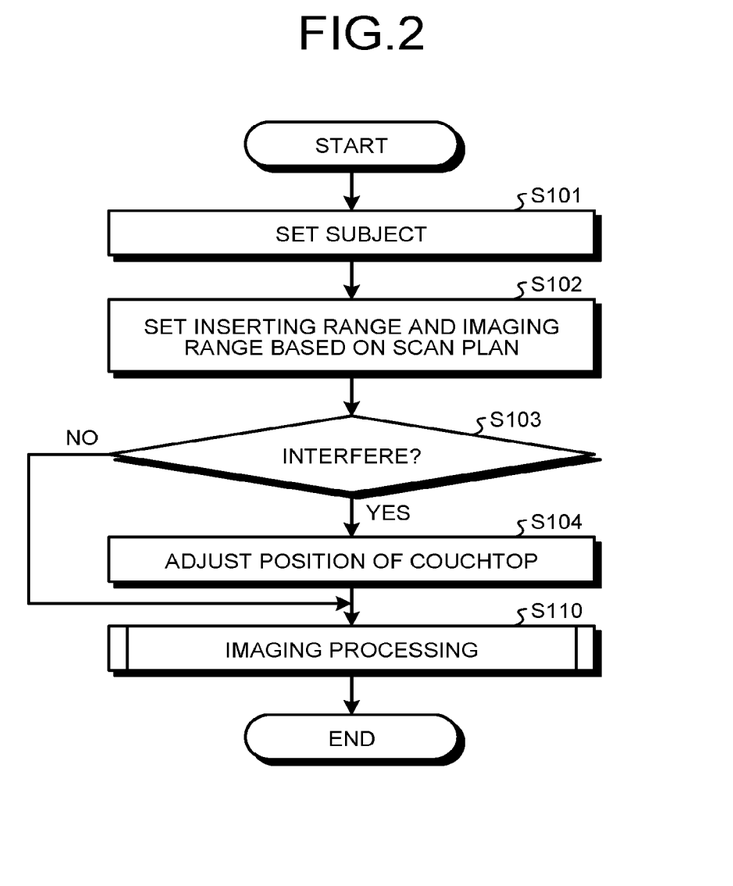
FIG. 2 is a flowchart showing procedures of processing performed by the X-ray CT apparatus according to the first embodiment.
Figure 3:
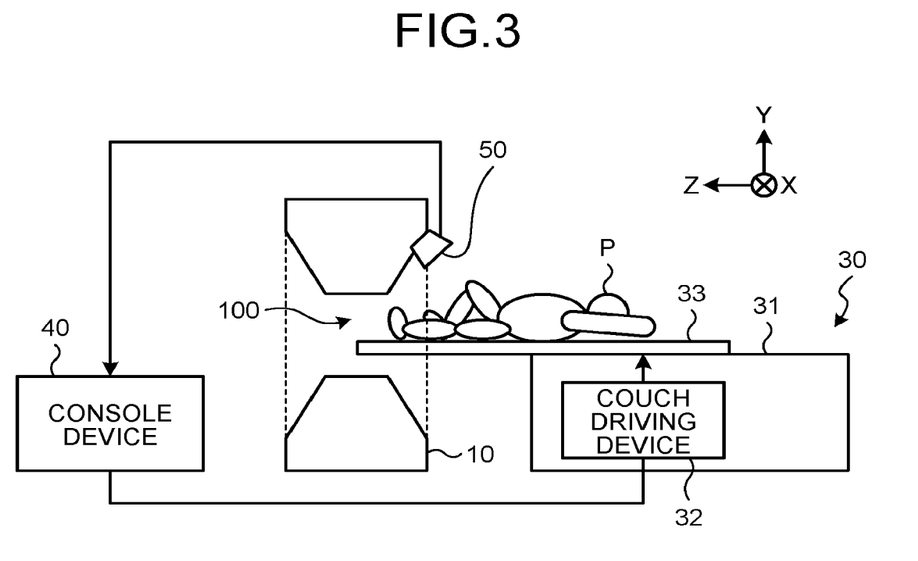
FIG. 3 is an illustration for explaining processing performed by the X-ray CT apparatus according to the first embodiment.

FIG. 2 is a flowchart showing procedures of processing performed by the X-ray CT apparatus 1 according to the first embodiment. FIG. 3 to FIG. 7 are illustrations for explaining the processing performed by the X-ray CT apparatus 1 according to the first embodiment.

At step S101 in FIG. 2, setting for the subject P is performed. Specifically, first, an operator, such as a clinical examination technician, performs an input operation to be a trigger for starting an examination by using the console device 40. At this time, the acquiring function 446 acquires patient information of a next examination based on the input operation received from the operator through the input interface 43, and displays the acquired patient information on the display 42. Next, the operator sets up a scan plan, for example, for imaging the abdomen of the subject P (patient) based on the patient information. In this case, for example, the operator lays the subject P on the couchtop 33 of the couch device 30 so that the subject P is inserted into the opening 100 of the gantry device 10 from the head or the feet. That is, the subject P is set on the couchtop 33. The setting orientation varies according to an examined portion or an examination purpose, and in the example illustrated in FIG. 3, the operator sets the subject P on the couchtop 33 such that the subject P is inserted into the opening 100 of the gantry device 10 from the feet.

Figure 4:
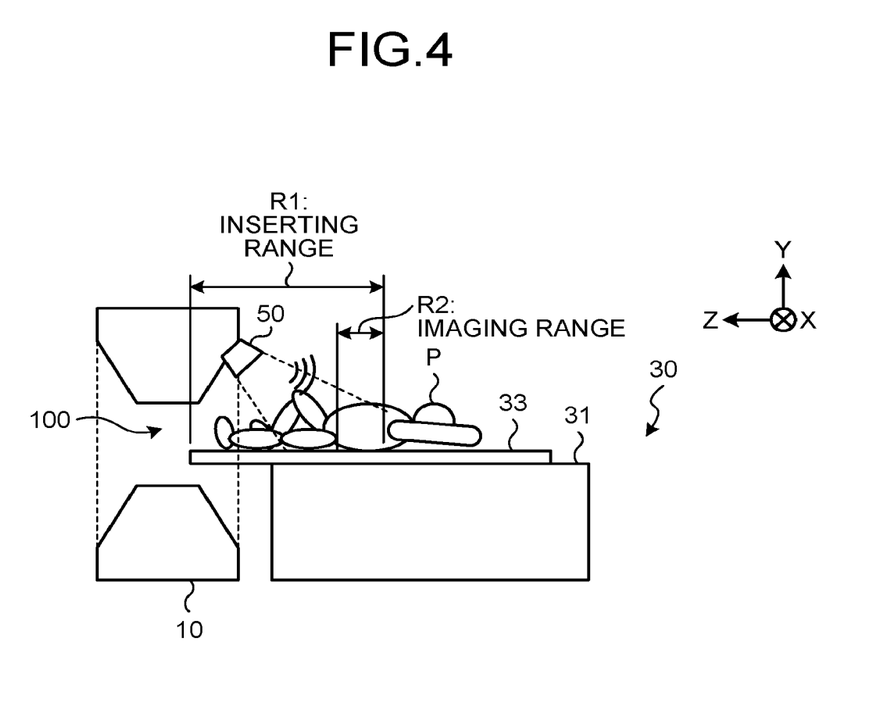
FIG. 4 is an illustration for explaining processing performed by the X-ray CT apparatus according to the first embodiment.

At step S102 in FIG. 2, an inserting range and an imaging range are set based on the scan plan. Specifically, as illustrated in FIG. 4, the operator determines an inserting range R1 that indicates a range in which the subject P is inserted to the opening 100 of the gantry device 10 by move of the couchtop 33 in a direction of body axis based on the scan plan. For example, the inserting range R1 indicates a range from an end of the couchtop 33 to the abdomen of the subject P. Moreover, the operator determines an imaging range R2 that indicates a range in which the subject P is imaged within the inserting range R1 based on the scan plan. For example, the imaging range R2 is included in the scan plan, and indicates a range including the abdomen of the subject P. The setting function 445 sets the inserting range R1 and the imaging range R2 determined by the operator based from the scan plan, based on the input operation received from the operator through the input interface 43. The inserting range R1 and the imaging range R2 may be determined automatically. For example, the gantry device 10 and the subject P on the couchtop 33 may be imaged by a camera arranged at a position from which the subject P can be observed on a plane from the side as shot image, and the setting function 445 may determine the inserting range R1 and the imaging range R2 automatically based on the shot image and a scan plan. The plane on which the subject P is observed from the side is, for example, a Z-Y plane.

The camera to image the gantry device 10 and the subject P on the couchtop 33 as shot image is arranged at a position at a position from which the subject P can be observed on a plane from the side, but it is not limited thereto. For example, the camera may be arranged at a position from which the subject P can be observed on a plane from above. The plane on which the subject P is observed from above is, for example, a Z-X plane.

Moreover, the camera may be provided in the gantry device 10 of the X-ray CT apparatus 1, may be arranged on a wall of an examination room in which the X-ray CT apparatus 1 is installed, or may be arranged on a ceiling of an examination room. For example, when the camera is arranged at a position from which the subject P can be observed on a plane from the side, it is arranged on a wall of the examination room. For example, when the camera is arranged at a position from which the subject P can be observed on a plane from above, it is arranged at the gantry device 10, or on the ceiling of the examination room.

At step S103 in FIG. 2, it is determined whether the subject P interferes with the gantry device 10 before the subject P is inserted into the opening 100 of the gantry device 10.

Figure 5:
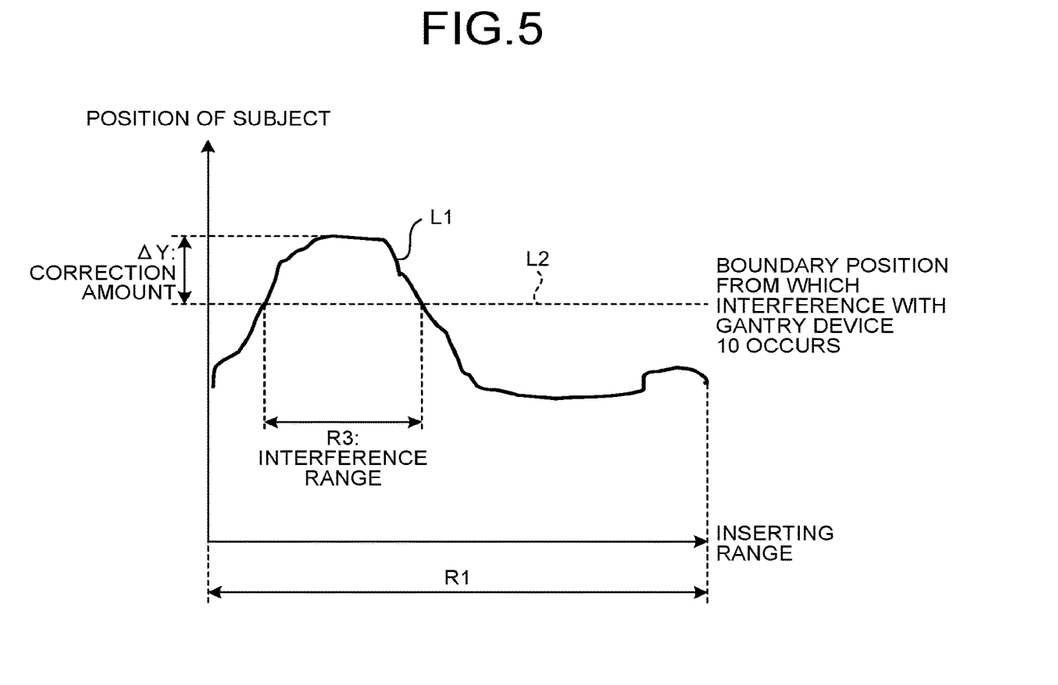
FIG. 5 is an illustration for explaining processing performed by the X-ray CT apparatus according to the first embodiment.

Specifically, first, the acquiring function 446 acquires subject position information L1 as illustrated in FIG. 5 from the position sensor 50 before the subject P is inserted into the opening 100 of the gantry device 10. The subject position information L1 indicates a position of the subject P in the inserting range R1. The position sensor 50 detects the position of the subject P, for example, from depth and the like, and outputs the detected position to the console device 40 as the subject position information L1. In the console device 40, the acquiring function 446 acquires the subject position information L1 output from the position sensor 50. The subject position information L1 is an example of the first position information.

Examples of the position sensor 50 include an ultrasonic sensor, an optical sensor, a magnetic sensor, and the like. Moreover, as long as the position of the subject P in the inserting range R1 can be detected from depth and the like, it is not limited to the position sensor 50 described above, and for example, a camera equipped with a depth sensor may be applied. Furthermore, as long as the position of the subject P in the inserting range R1 can be detected from depth and the like, a position at which the position sensor 50 is arranged is not limited. The number of the position sensor 50 to be provided is not limited, and the acquiring function 446 may acquire the subject position information L1 from plural units of the position sensors 50. Moreover, the orientation of the position sensor 50 may be changeable as necessary.

Next, the determining function 447 determines whether the subject P interferes with the gantry device 10 based on the subject position information L1 acquired by the acquiring function 446. Specifically, the determining function 447 has recognized the current position of the couchtop 33, and recognizes height of the subject P from the couchtop 33 from the subject position information L1 acquired by the acquiring function 446. Moreover, the determining function 447 has recognized the position of the opening 100 of the gantry device 10 as opening position information, and determines whether the subject P interferes with the gantry device 10 by using the subject position information L1 acquired by the acquiring function 446 and the opening position information. The opening position information is an example of second position information.

When it is determined that the subject P does not interfere with the gantry device 10 based on the result of determination (step S103: NO), step S110 in FIG. 2 is performed.

On the other hand, when it is determined that the subject P interferes with the gantry device 10 (step S103 YES), step S104 in FIG. 2 is performed. Specifically, suppose that the subject P bends his/her leg (for example, right leg) after the operator sets the subject P on the couchtop 33, or that the subject P cannot bend his/her right leg. In this case, as shown in FIG. 5, the subject position information L1 acquired by the acquiring function 446 indicates that the position of the right leg, particularly, the position of the right knee of the subject P is at the highest position. The determining function 447 compares the subject position information L1 acquired by the acquiring function 446 and the opening position information L2 shown in FIG. 5. The opening position information L2 indicates, for example, a boundary position from which the subject P interferes with the gantry device 10 in the Y-axis direction. The determining function 447 detects an interference range R3 that indicates a range in which the right leg of the subject P interferes with the gantry device 10 based on the result of comparison between the subject position information L1 and the opening position information L2. In this case, the determining function 447 determines that the subject P interferes with the gantry device 10, and step S104 in FIG. 2 is performed.

Figure 6:
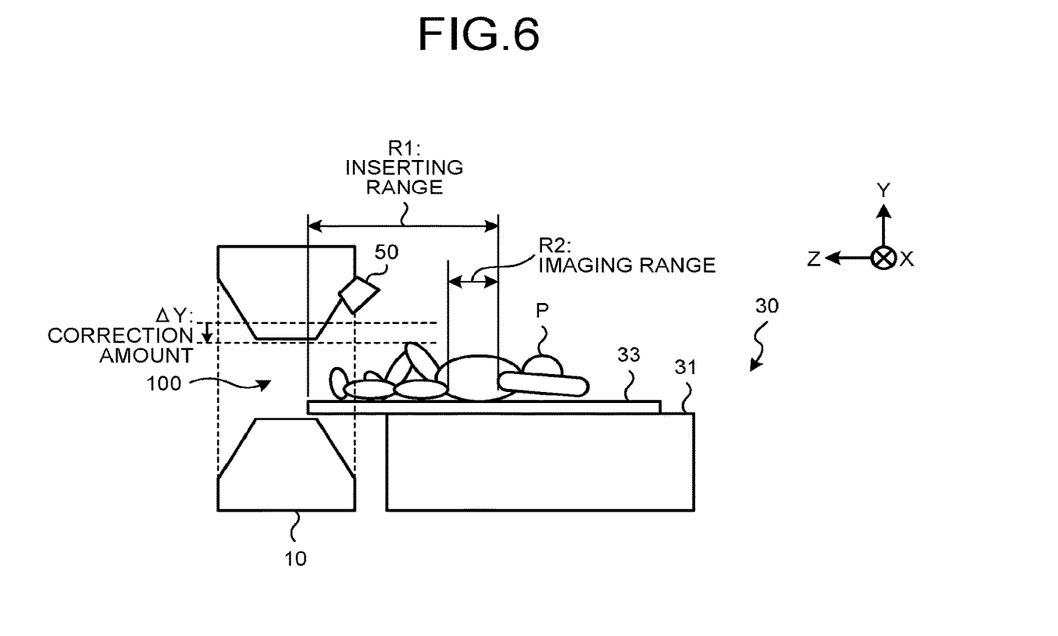
FIG. 6 is an illustration for explaining processing performed by the X-ray CT apparatus according to the first embodiment.

At step S104 in FIG. 2, adjustment of the position of the couchtop 33 is performed. Specifically, when determining that the subject P interferes with the gantry device 10, the determining function 447 determines a correction amount $\Delta Y$ to avoid the interference based on the subject position information L1 and the opening position information L2. The correction amount $\Delta Y$ is a correction amount in the Y-axis direction in the interference range R3, and corresponds to a maximum value of difference between the position of the right leg of the subject P indicated by the subject position information L1 and the boundary position indicated by the opening position information L2. In this case, as illustrated in FIG. 6, the determining function 447 adjusts the position of the couchtop 33 based on the determined correction amount $\Delta Y$. Specifically, the determining function 447 controls the couch driving device 32 of the couch device 30 such that the position of the couchtop 33 is moved downward by the correction amount $\Delta Y$.

Figure 7:
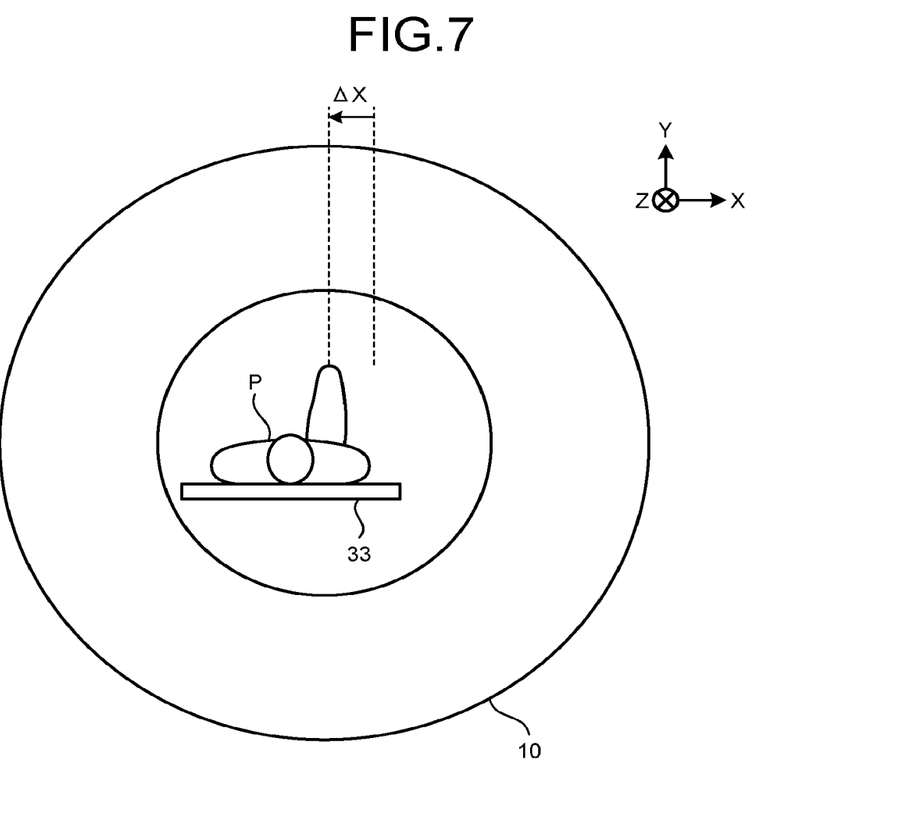
FIG. 7 is an illustration for explaining processing performed by the X-ray CT apparatus according to the first embodiment.

The determining function 447 adjusts the position of the couchtop 33 in the Y-axis direction (up-and-down direction) when determining that the subject P interferes with the gantry device 10, but it is not limited thereto. The determining function 447 may adjust the position of the couchtop 33 in the X-axis direction (left-and-right direction). For example, when determining that the subject P interferes with the gantry device 10, the determining function 447 may determine the correction amount $\Delta X$ to adjust in the X-axis direction to avoid the interference based on the subject position information L1 and the opening position information L2. The determining function 447 then adjusts the position of the couchtop 33 based on the determined correction amount $\Delta X$ as illustrated in FIG. 7. Specifically, the determining function 447 controls the couch driving device 32 of the couch device 30 such that the position of the couchtop 33 is moved laterally by the correction amount $\Delta X$. Furthermore, the determining function 447 only applies adjustment of the position of the couchtop 33 to one direction out of the Y-axis direction and the X-axis direction but, not limited thereto, may also apply adjustment of the position of the couchtop 33 to both of the Y-axis direction and the X-axis direction.

Figure 8:
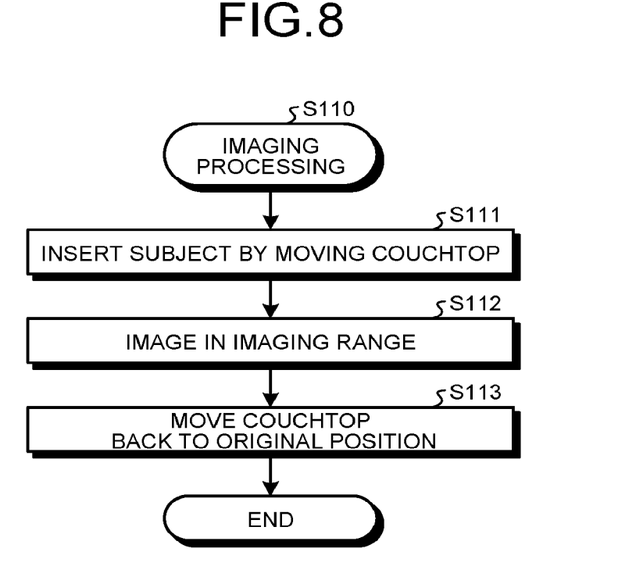
FIG. 8 is a flowchart showing procedures of imaging processing in the first embodiment.

FIG. 8 is a flowchart showing procedures of imaging processing (step S110) in the first embodiment.

At step S111 in FIG. 8, by moving the couchtop 33, the subject P is inserted in to the opening 100 of the gantry device 10. Specifically, the scan control function 441 controls the couch driving device 32 of the couch device 30 based on an input operation received from the operator through the input interface 43, to move the couchtop 33 on which the subject P is laid, thereby inserting the subject P into the opening 100 of the gantry device 10.

At step S112 in FIG. 8, imaging is performed in the imaging range R2. Specifically, the scan control function 441 controls the gantry device 10 such that imaging is performed in the imaging range R2. That is, the scan control function 441 performs scan control with respect to the gantry device 10.

At step S113 in FIG. 8, the couchtop 33 is moved back to its original position. Specifically, the scan control function 441 controls the couch driving device 32 of the couch device 30 based on an input operation received from the operator through the input interface 43, to move the couchtop 33 back to the original position.

As described above, in the X-ray CT apparatus 1 according to the first embodiment, first, the setting function 445 sets the inserting range that indicates an inserting range in which the subject P is inserted into the opening 100 of the gantry device 10 by move of the couchtop 33 of the couch device 30, and the imaging range in which the subject P is imaged within the inserting range, based on a scan plan. Before the subject P is inserted in to the opening 100 of the gantry device 10, the acquiring function 446 acquires the position of the subject P in the inserting range as the subject position information L1. The determining function 447 determines whether the subject P interferes with the gantry device 10 based on the subject position information L1 and the opening position information L2 indicating the position of the opening 100 of the gantry device 10, and adjusts the position of the couchtop 33 based on the result of determination. As described, in the X-ray CT apparatus 1 according to the first embodiment, even if the position of the subject P changes as the subject P moves before the subject P is inserted into the opening 100 of the gantry device 10, the position of the couchtop 33 is adjusted, when it is determined that the subject P interferes with the gantry device 10, based on the result of determination. Therefore, in the X-ray CT apparatus 1 according to the first embodiment, it is possible to prevent suspension of imaging or retake caused by interference between the subject P and the gantry device 10, and to reduce unnecessary exposure.

Second Embodiment

In a second embodiment, a case in which a range of interference is notified when it is determined that the subject P interferes with the gantry device 10 will be described. In the following, processing that differs from the first embodiment will be mainly explained in the second embodiment.

Figure 9:
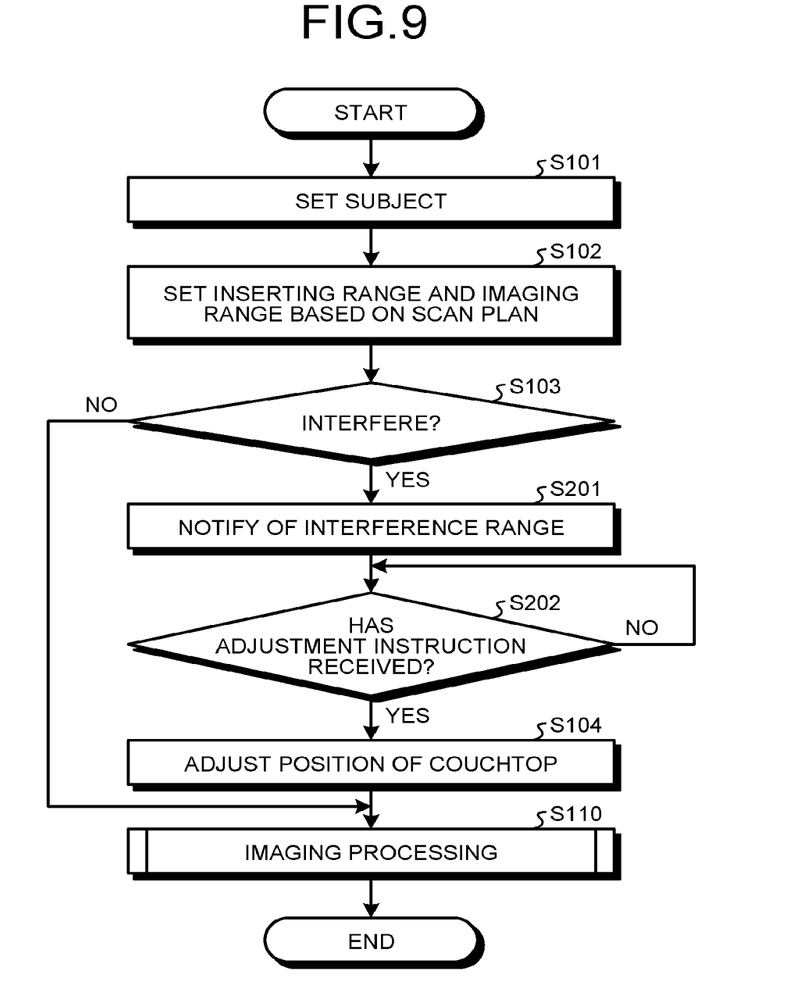
FIG. 9 is a flowchart showing procedures of processing performed by an X-ray CT apparatus according to a second embodiment.
Figure 10:
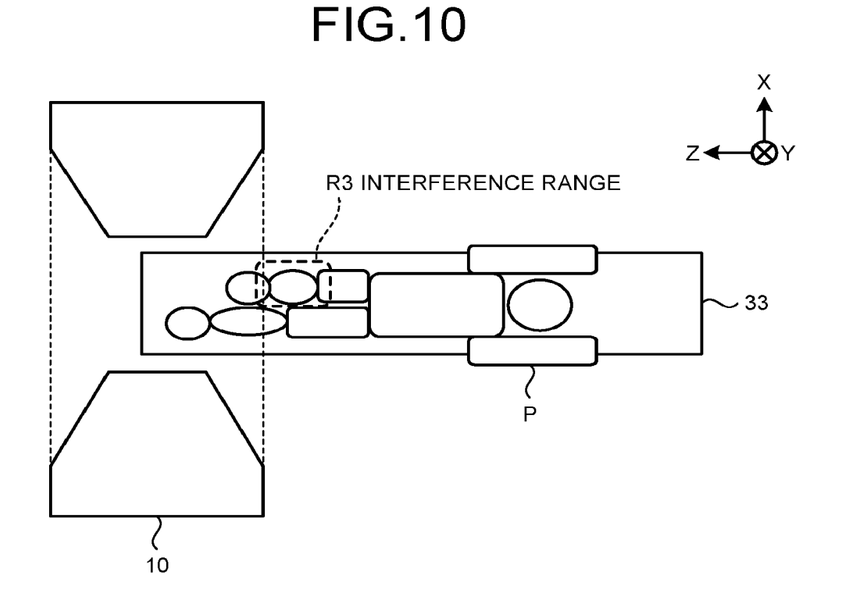
FIG. 10 is an illustration for explaining processing performed by the X-ray CT apparatus according to the second embodiment.

FIG. 9 is a flowchart showing procedures of processing performed by the X-ray CT apparatus 1 according to the second embodiment. FIG. 10 is an illustration for explaining processing performed by the X-ray CT apparatus 1 according to the second embodiment.

First, in FIG. 9, steps S101 to S103 similar to those in FIG. 2 are performed. At step S103, it is determined whether the subject P interferes with the gantry device 10 before the subject P is inserted into the opening 100 of the gantry device 10. When it is found that the subject P interferes with the gantry device 10 as a result of determination (step S103: YES), step S201 in FIG. 9 is performed.

At step S201 in FIG. 9, an interference range is notified. Specifically, in the console device 40, the display control function 444 displays the range of interference on the display 42 when it is determined that the subject P interferes with the gantry device 10, thereby notifying the operator that the subject P interferes with the gantry device 10. For example, the display control function 444 notifies the operator by displaying an image illustrated in FIG. 10 on the display 42 as a display image. As illustrated in FIG. 10, for example, the display image shows the gantry device 10, the subject P on the couchtop 33, and the interference range R3 detected by the determining function 447. Specifically, for example, an image of the gantry device 10 and the subject P on the couchtop 33 are taken by a camera arranged at a position from which the subject P can be observed on a plane from above as a shot image, and the display control function 444 displays an image in which an image showing the interference range R3 is superimposed thereon at a position of the right leg of the subject P in the shot image on the display 42 as the display image, thereby notifying the operator. The plane on which the subject P can be observed from above is, for example, the Z-X plane. Alternatively, a schematic diagram of the gantry device 10 and the subject P on the couchtop 33 observed on a plane from above may be prepared as a sample image, and the display control function 444 may display an image in which the interference range R3 is superimposed thereon at the position of the right leg of the subject P in the sample image on the display 42 as the display image, thereby notifying the operator.

AT step S202 in FIG. 9, it is determined whether an adjustment instruction has been received. For example, the determining function 447 waits for reception of an adjustment instruction from the operator (step S202: NO), and receives the adjustment instruction from the operator through the input interface 43 (step S202: YES). In this case, in FIG. 9, steps S104, S110 similar to those in FIG. 2 are performed.

As described above, in the X-ray CT apparatus 1 according to the second embodiment, when it is determined that the subject P interferes with the gantry device 10 before the subject P is inserted in to the opening 100 of the gantry device 10, the interference range R3 in which interference occurs is notified to the operator. Therefore, in the X-ray CT apparatus 1 according to the second embodiment, it is possible to prevent suspension of imaging or retake caused by interference between the subject P and the gantry device 10, and to reduce unnecessary exposure.

Third Embodiment

In a third embodiment, a case in which it is determined that the subject P interferes with the gantry device 10 during the course of insertion of the subject P into the opening 100 of the gantry device 10 in the imaging processing (step S110) will be described. In the following, processing that differs from the first and the second embodiments will be mainly explained in the third embodiment.

Figure 11:
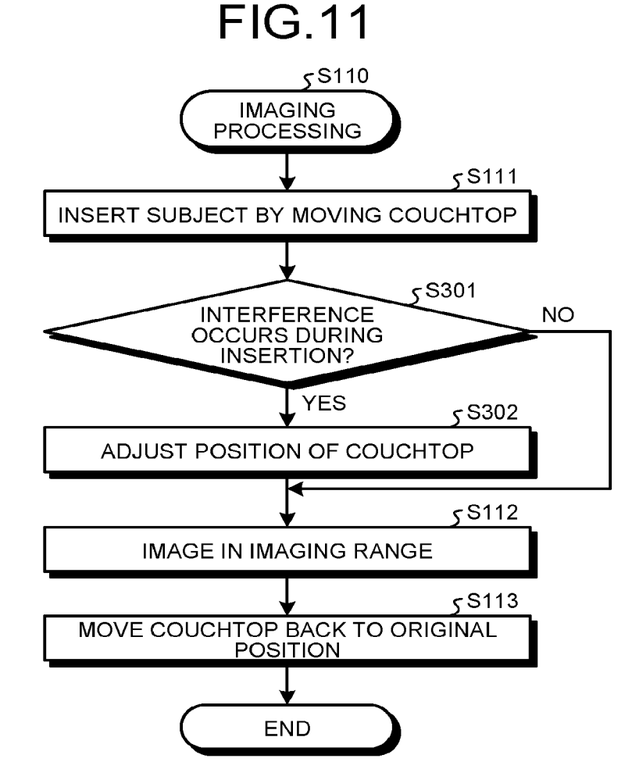
FIG. 11 is a flowchart showing procedures of imaging processing in a third embodiment.

FIG. 11 is a flowchart showing procedures of the imaging processing (step S110) in the third embodiment.

First, in FIG. 11, step S111 similar to that in FIG. 8 is performed. At step S111, the couchtop 33 is moved to insert the subject P into the opening 100 of the gantry device 10.

At step S301 in FIG. 11, it is determined whether interference occurs during insertion. Specifically, the acquiring function 446 acquires the subject position information L1 from the position sensor 50 also during the course of insertion of the subject P into the opening 100 of the gantry device 10. The determining function 447 determines whether the subject P interferes with the gantry device 10 based on the subject position information L1 acquired by the acquiring function 446 during this process.

When it is found that the subject P does not interfere with the gantry device 10 as a result of determination (step S301: NO), step S112, S113 similar to those in FIG. 8 are performed in FIG. 11.

On the other hand, when it is found that the subject P interferes with the gantry device 10 as a result of determination (step S301 YES), step S302 in FIG. 11 is performed.

At step S302 in FIG. 11, adjustment of the position of the couchtop 33 is performed. Specifically, when determining that the subject P interferes with the gantry device 10, the determining function 447 determines a correction amount to avoid the interference based on the subject position information L1 and the opening position information. The determining function 447 adjusts the position of the couchtop 33 based on the determined correction amount. Specifically, the determining function 447 controls the couch driving device 32 of the couch device 30 such that the position of the couchtop 33 is adjusted by the correction amount. Thereafter, in FIG. 11, steps S112, S113 similar to those in FIG. 8 are performed.

As described above, in the X-ray CT apparatus 1 according to the third embodiment, the position of the couchtop 33 is adjusted, when it is further determined that the subject P interferes with the gantry device 10, during the course of insertion of the subject P into the opening 100 of the gantry device 10, based on the result of determination. Therefore, in the X-ray CT apparatus 1 according to the third embodiment, it is possible to prevent suspension of imaging or retake caused by interference between the subject P and the gantry device 10, and to reduce unnecessary exposure.

Fourth Embodiment

In a fourth embodiment, a case in which it is determined whether the imaging range R2 falls off an imaging-enabled range in the opening 100 of the gantry device 10 as a result of adjustment of the position of the couchtop 33 when it is determined that the subject P interferes with the gantry device 10 during the course of insertion of the subject P into the gantry device 10 in the imaging processing (step S110) will be described. In the following, processing that differs from the third embodiment will be mainly explained in the fourth embodiment.

Figure 12:
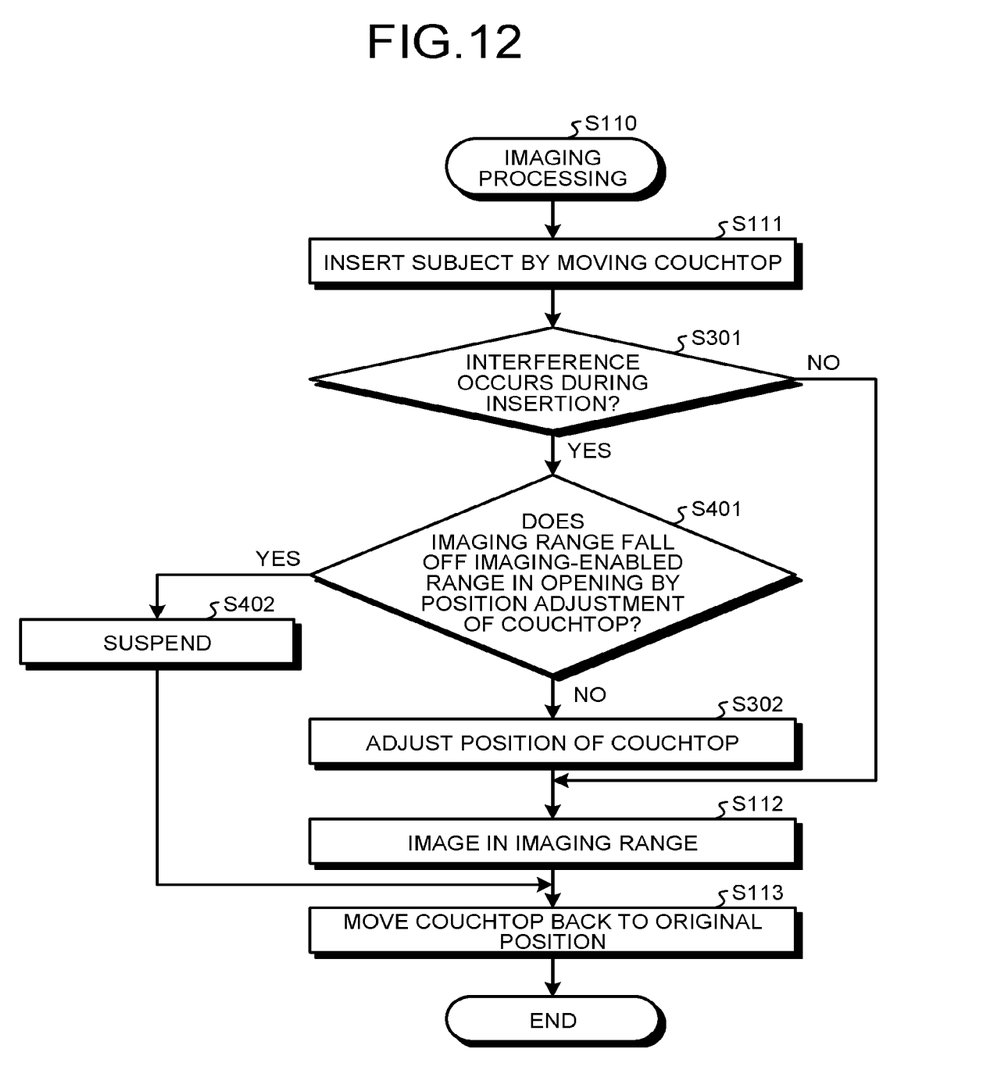
FIG. 12 is a flowchart showing procedures of imaging processing in a fourth embodiment.
Figure 13:
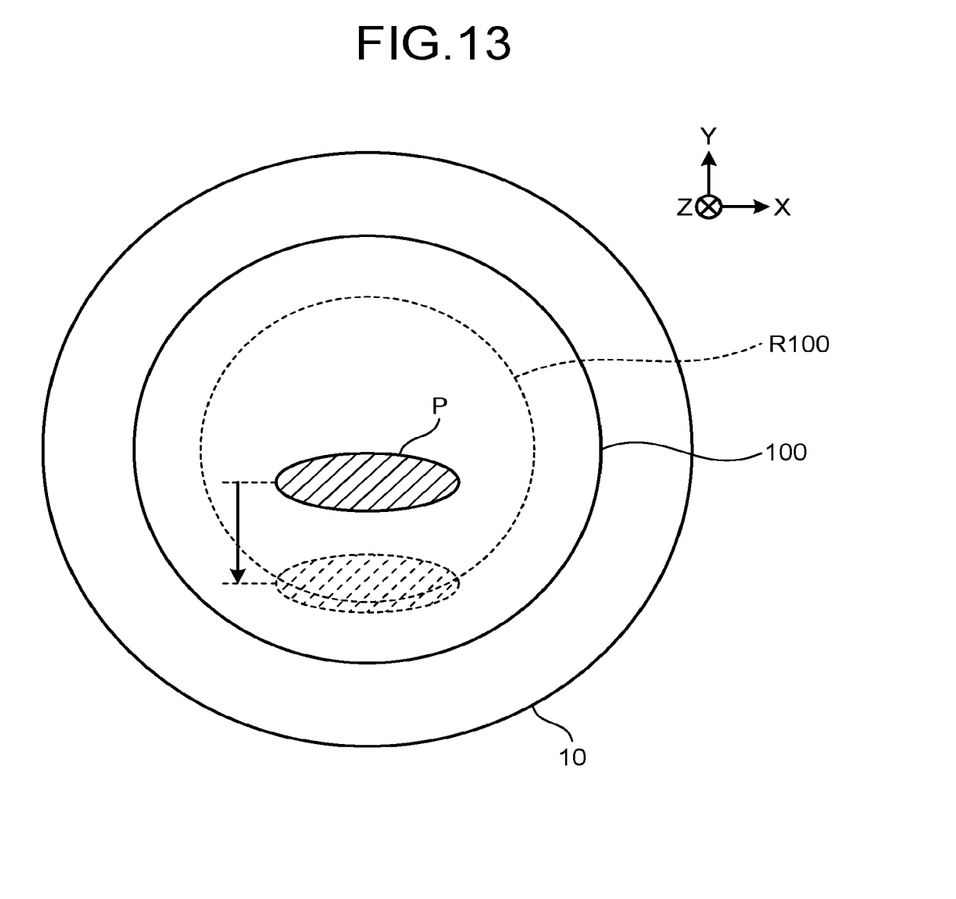
FIG. 13 is an illustration for explaining processing performed by an X-ray CT apparatus according to the fourth embodiment.

FIG. 12 is a flowchart showing procedures of the imaging processing (step S110) in the fourth embodiment. FIG. 13 is an illustration for explaining processing performed by the X-ray CT apparatus 1 according to the fourth embodiment.

First, in FIG. 12, steps S111, S301 similar to those in FIG. 11 are performed. At step S301, it is determined whether interference occurs during insertion. When it is found that the subject P interferes with the gantry device 10 as a result of determination (step S301 YES), step S401 in FIG. 12 is performed.

At step S401 in FIG. 12, it is determined whether the imaging range R2 falls off an imaging-enabled range in the opening 100 of the gantry device 10 as a result of adjustment of the position of the couchtop 33. Specifically, the determining function 447 determines, when determining that the subject P interferes with the gantry device 10, the correction amount to avoid the interference based on the subject position information L1 and the opening position information. The determining function 447 then determines, when adjusting the position of the couchtop 33 based on the determined correction amount, whether the imaging range R2 falls off an imaging-enabled range R100 (refer to FIG. 13) in the opening 100 as a result of adjustment of the position of the couchtop 33.

When the imaging range R2 falls off the imaging-enabled range R100 in the opening 100 as a result of adjustment of the position of the couchtop 33 (step S401: YES), step S402 in FIG. 11 is performed.

At step S402 in FIG. 12, insertion is suspended. Specifically, the determining function 447 controls the couch driving device 32 of the couch device 30 to suspend the insertion of the subject P when the imaging range R2 falls off the imaging-enabled range in the opening 100 as a result of adjustment of the position of the couchtop 33. Thereafter, in FIG. 12, step S113 similar to that in FIG. 11 is performed.

On the other hand, when it is found, as a result of determination, that the imaging range R2 falls within the imaging-enabled range R100 in the opening 100 after adjustment of the position of the couchtop 33 (step S401: NO), steps S302, S112, S113 similar to those in FIG. 11 are performed in FIG. 12.

As described above, in the X-ray CT apparatus 1 according to the fourth embodiment, when it is determined that the subject P interferes with the gantry device 10 during the course of insertion of the subject P into the opening 100 of the gantry device 10, if the imaging range R2 falls off the imaging-enabled range R100 in the opening 100 of the gantry device 10 as a result of adjustment of the position of the couchtop 33, insertion of the subject P is suspended. On the other hand, when the imaging range R2 falls within the imaging-enabled range R100 in the opening 100 after adjustment of the position of the couchtop 33, the position of the couchtop 33 is adjusted based on a result of determination that the subject P interferes with the gantry device 10. Therefore, in the X-ray CT apparatus 1 according to the fourth embodiment, it is possible to prevent suspension of imaging or retake caused by interference between the subject P and the gantry device 10, and to reduce unnecessary exposure.

Other Embodiments

The first to the fourth embodiments have been described hereinabove, but various other embodiments other than the first to the fourth embodiments described above may be implemented.

In the above embodiments, the subject P is inserted into the opening 100 of the gantry device 10 by move of the subject P, but embodiments are not limited thereto. For example, the subject P may be inserted into the opening 100 of the gantry device 10 by move of the gantry device 10. Moreover, the present embodiment is applicable to an X-ray CT apparatus that does not include the couch device 30 on which the subject P is laid, such as an upright CT apparatus.

In the above embodiments, when it is determined that the subject P interferes with the gantry device 10, the display control function 444 notifies of a range of the interference, but embodiments are not limited thereto. For example, the display control function 444 may notify that the subject P interferes with the gantry device 10 to an operator by display of a message or the like on the display 42, or by voice output.

The above embodiments have been described using the X-ray CT apparatus 1 as an example of a modality apparatus, but not only to the X-ray CT apparatus 1, it may be applied also to other modality apparatuses, such as an MRI apparatus and a nuclear-medicine diagnostic apparatus (for example, positron emission tomography (PET) apparatus).

Furthermore, the processing circuitry 44 may implement the function by using a processor of an external device connected through a network. For example, the processing circuitry 44 implements the respective functions illustrated in FIG. 1 by reading and executing programs corresponding to the respective functions from the memory 41, and by using an external workstation that is connected to the X-ray CT apparatus 1 through a network or a cloud as computational resources.

The respective components of the respective devices according to the embodiments described above are of functional concept, and it is not necessarily required to be configured physically as illustrated. That is, specific forms of distribution and integration of the respective devices are not limited to the ones illustrated, and all or a part thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Moreover, the control method described in the above embodiments can be implemented by executing a program that has been prepared in advance by a computer such as a personal computer and a workstation. This control program can be distributed through a network such as the Internet. Furthermore, this control program can be recorded on a computer-readable recording medium, such as a hard disk, a flexible disk (FD), a compact-disk read-only memory (CD-ROM), a magneto optical disk (MO), and a digital versatile disk (DVD), and can be executed by being read by a computer from the recording medium.

According to at least one of the embodiments described above, interference between a subject and a gantry device can be prevented.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical diagnostic-imaging apparatus comprising:
    a gantry device that includes an opening into which a subject is inserted; and
    processing circuitry configured:
        to set an inserting range indicating a range in which the subject is inserted into the opening by any one of move of the subject and move of the gantry device,
        to acquire a position of the subject in the inserting range as first position information, and
        to determine whether the subject interferes with the gantry device based on the first position information.

2. The medical diagnostic-imaging apparatus according to claim 1, wherein
    the processing circuitry is configured to adjust a position of a couchtop on which the subject is laid based on a result of the determination.

3. The medical diagnostic-imaging apparatus according to claim 1, wherein
    the processing circuitry is configured to notify, when it is determined that the subject interferes with the gantry device, of a range of interference, or notify that the subject interferes with the gantry device.

4. The medical diagnostic-imaging apparatus according to claim 1, wherein
the inserting range indicates a range in which the subject is inserted into the opening by move of a couchtop on which the subject is laid.

5. The medical diagnostic-imaging apparatus according to claim 4, wherein the processing circuitry is configured
to determine whether the subject interferes with the gantry device based on the first position information and second position information indicating a position of the opening,
to determine, when determining that the subject interferes with the gantry device, a correction amount to avoid interference based on the first position information and the second position information, and
to adjust a position of the couchtop based on the correction amount.

6. The medical diagnostic-imaging apparatus according to claim 4, wherein before the subject is inserted into the opening,
the processing circuitry is configured
to acquire the first position information,
to determine whether the subject interferes with the gantry device based on the first position information, and
to adjust a position of the couchtop based on a result of determination.

7. The medical diagnostic-imaging apparatus according to claim 6, wherein also during a course of insertion of the subject into the opening,
the processing circuitry is configured
to acquire the first position information,
to determine whether the subject interferes with the gantry device based on the first position information, and
to adjust the position of the couchtop based on a result of determination.

8. The medical diagnostic-imaging apparatus according to claim 7, wherein the processing circuitry is configured
to determine, when determining that the subject interferes with the gantry device, whether an imaging range included in a scan plan falls off an imaging-enabled range in the opening as a result of adjustment of the position of the couchtop, and
to suspend insertion of the subject when the imaging range falls off the imaging-enabled range in the opening as a result of the adjustment of the position of the couchtop.

9. The medical diagnostic-imaging apparatus according to claim 8, wherein the processing circuitry is configured to adjust the position of the couchtop when the imaging range falls within the imaging-enabled range in the opening after the adjustment of the position of the couchtop.

10. The medical diagnostic-imaging apparatus according to claim 1, wherein the processing circuitry is configured to adjust a position of a couchtop on which the subject is laid in each of at least two orthogonal directions based on a result of the determination.

11. The medical diagnostic-imaging apparatus according to claim 1, wherein the processing circuitry is configured to receive sensor information from a sensor to acquire the position of the subject in the inserting range.

12. The medical diagnostic-imaging apparatus according to claim 1, wherein the processing circuitry is configured to determine whether a height of a part of the subject is above a boundary position of an opening in the apparatus into which the subject is to be inserted.

13. The medical diagnostic-imaging apparatus according to claim 1, wherein the processing circuitry is configured to determine whether any part of the subject is outside of a boundary position of an opening in the apparatus into which the subject is to be inserted.

* * * * *